(12) United States Patent
Stangel et al.

(10) Patent No.: US 10,966,809 B2
(45) Date of Patent: Apr. 6, 2021

(54) METHOD AND DEVICE FOR TREATING CARIES USING LOCALLY DELIVERED MICROWAVE ENERGY

(71) Applicant: BIOMAT SCIENCES, Bethesda, MD (US)

(72) Inventors: Ivan Stangel, Bethesda, MD (US); Marguerite A. Sognier, Houston, TX (US); George D. Arndt, Friendswood, TX (US); Diane L. Byerly, Seabrook, TX (US); John Dusl, Houston, TX (US)

(73) Assignee: THE UNITED STATES OF AMERICA AS REPRESENTED BY THE ADMINISTRATOR OF THE NATIONAL AERONAUTICS AND SPACE ADMINISTRATION, Washington, DC (US)

( * ) Notice: Subject to any disclaimer, the term of this patent is extended or adjusted under 35 U.S.C. 154(b) by 0 days.

(21) Appl. No.: 14/765,550

(22) PCT Filed: Feb. 3, 2014

(86) PCT No.: PCT/US2014/014500
§ 371 (c)(1),
(2) Date: Aug. 3, 2015

(87) PCT Pub. No.: WO2014/121229
PCT Pub. Date: Aug. 7, 2014

(65) Prior Publication Data
US 2015/0374471 A1 Dec. 31, 2015

Related U.S. Application Data

(60) Provisional application No. 61/760,012, filed on Feb. 1, 2013.

(51) Int. Cl.
*A61C 19/06* (2006.01)
*A61C 17/02* (2006.01)
(Continued)

(52) U.S. Cl.
CPC .............. *A61C 19/06* (2013.01); *A61C 17/02* (2013.01); *A61N 5/022* (2013.01); *A61N 5/045* (2013.01); *A61C 1/08* (2013.01)

(58) Field of Classification Search
CPC ........... A61C 19/04; A61C 17/02; A61C 1/08; A61C 1/088; A61C 19/06; A61N 5/022;
(Continued)

(56) References Cited

U.S. PATENT DOCUMENTS 3,753,651 A * 8/1973 Boucher .................. A61L 2/12
219/738
4,446,874 A * 5/1984 Vaguine .................. A61N 5/04
219/696

(Continued)

FOREIGN PATENT DOCUMENTS

EP 0392951 A2 4/1990
RU 83418 U1 6/2009

*Primary Examiner* — Sean M Michalski
*Assistant Examiner* — Shannel N Wright
(74) *Attorney, Agent, or Firm* — Blue Filament Law PLLC

(57) ABSTRACT

A method and a device for treating dental caries using microwave energy applied directly to teeth at frequencies that are lethal to the bacteria in caries, without being destructive to tooth tissues. The method and a device will have a significant economic and health impact, leading to a reduction in traditional surgical interventions, as well by improving access to care for those with health disparities.

11 Claims, 8 Drawing Sheets

(51) Int. Cl.
*A61N 5/02* (2006.01)
*A61N 5/04* (2006.01)
*A61C 1/08* (2006.01)

(58) Field of Classification Search
CPC .......... A61N 5/045; A61N 5/02; A61N 5/065; A61N 2005/0606
See application file for complete search history.

(56) References Cited

U.S. PATENT DOCUMENTS

| | | | | |
|---|---|---|---|---|
| 4,600,018 A * | 7/1986 | James | ................. | A61N 1/06 343/700 MS |
| 5,026,959 A * | 6/1991 | Ito | ................. | A61B 18/18 219/690 |
| 5,207,231 A * | 5/1993 | Fakhri | ................. | A61N 1/0472 607/134 |
| 5,421,727 A * | 6/1995 | Stevens | ................. | A61C 5/40 433/102 |
| 6,083,218 A * | 7/2000 | Chou | ................. | A61C 1/0046 433/215 |
| 6,223,085 B1 * | 4/2001 | Dann | ................. | A61B 18/1492 606/29 |
| 6,254,389 B1 * | 7/2001 | Seghatol | ................. | A61C 5/00 433/215 |
| 6,319,007 B1 * | 11/2001 | Livaditis | ................. | A61B 18/1402 433/224 |
| 6,571,049 B1 * | 5/2003 | Nath | ................. | A61C 1/08 250/504 H |
| 7,144,248 B2 * | 12/2006 | Irwin | ................. | A61N 5/0603 362/572 |
| 7,713,294 B2 * | 5/2010 | Bornstein | ................. | A61L 2/084 607/88 |
| 7,744,592 B2 * | 6/2010 | Hoenig | ................. | A61N 5/04 606/33 |
| 2002/0106605 A1 * | 8/2002 | Seghatol | ................. | A61C 5/00 433/29 |
| 2009/0022811 A1 * | 1/2009 | LeGeros | ................. | A61F 2/2846 424/602 |
| 2009/0130622 A1 * | 5/2009 | Bollinger | ................. | A61C 1/0046 433/29 |
| 2010/0097284 A1 * | 4/2010 | Brannan | ................. | A61B 18/18 343/793 |
| 2010/0109966 A1 * | 5/2010 | Mateychuk | ................. | A61N 1/37229 343/841 |
| 2013/0022936 A1 * | 1/2013 | Flanagan | ................. | A61C 5/04 433/29 |
| 2015/0044632 A1 * | 2/2015 | Bergheim | ................. | A61C 17/028 433/82 |

* cited by examiner

METHOD AND DEVICE FOR TREATING CARIES USING LOCALLY DELIVERED MICROWAVE ENERGY

RELATED APPLICATIONS

This application claims priority benefit of U.S. Provisional Application Ser. No. 61/760,012 filed Feb. 3, 2013; the contents of which are hereby incorporated by reference in their entirety.

STATEMENT OF GOVERNMENT INTEREST

This invention was made in part with Government support under grant number 1215100 from the National Science Foundation and in collaboration with NASA at the Johnson Space Center. The invention described herein may be manufactured and used by or for U.S. Government purposes without the payment.

FIELD OF THE INVENTION

The present invention is in the technical field of dentistry and in particular to the present invention is for the treatment of caries by microwave irradiation.

BACKGROUND OF THE INVENTION

Caries is a multi-factorial disease that involves prolonged colonization of acid-producing bacteria on teeth. Fermentation of dietary carbohydrates by caries leads to a localized drop in pH below a critical value of 5.5, resulting in the demineralization of enamel and potentially damaging underlying tooth structure. Mutans streptococci (*Streptococcus mutans* and *Streptococcus sobrinus*) have consistently been shown to be the prominent acid-producing group that is responsible for the development of caries, with lactobacilli species being found in deeper caries progression. In the case of secondary caries (the most prevalent reason for failure of fillings), the bacteria are dominated by *Streptococcus* spp., *Actinomyces* spp., and *Lactobacillus* spp. Thus, managing these species is a key factor in treating either primary or recurrent caries and promoting remineralization.

If left untreated, caries can lead to the progressive destruction of tooth structure, pain, tooth loss, loss of oral function, as well as have systemic health consequences. Although advances have been made in managing caries using non- or minimally-invasive procedures, the overwhelming preponderance of interventions made by dentists for the treatment of caries involves surgical intervention using rotary instrumentation (a "drill"). Following the surgical excision of the diseased portion of a tooth, various materials are then used to reconstruct it (a "filling"). In this traditional "drill and fill" surgical management of caries, which has been the standard of care since the 19th century, access to caries almost always involves the removal of healthy tooth tissue. In addition to this functional and biological cost, a traditional surgical approach has a vast economic impact on health expenditures. While the continuum of caries treatment runs from complete surgical removal with tooth restoration to partial removal and sealing, to sealing only, to leaving existing caries intact and attempting only to promote remineralization via various strategies. With the exception of the first approach, none of these other strategies is completely effective for the treatment of primary caries, as there is reliance on either patient compliance for biofilm management or on the sealing of lesions using restorative materials.

Although various reviews indicate that sealing arrests in situ lesions, its effectiveness is limited by the inability of composite resin restorative materials to perfectly seal a cavity preparation. Clinical trials have confirmed this finding, with caries having been shown to progress in significant numbers of sealed teeth. Thus, the lack of reliable effectiveness combined with the prior discussed factors will preclude many practitioners from adopting conservative approaches for the treatment of caries. The likelihood remains high that dentists will continue to rely on surgical interventions to completely control caries in teeth.

Thus, there exists a need for more effective and practical approaches for the care and elimination of dental caries that can lead to less costly intervention, and lead need to greater integration of less invasive procedures for the treatment dental caries.

SUMMARY OF THE INVENTION

A method of irradiating a tooth with microwave energy using a microwave generator, a flexible wave guide and an antenna is provided, where the antenna makes contact with the tooth to irradiate the tooth, and where dielectric properties of the antenna are matched with those of the tooth. The reflected microwave energy is at least 80 to 100%, and in certain embodiments 90 to 98% of the radiated energy when the antenna is not in contact with the tooth. The irradiated microwave energy kills bacteria within the field of irradiation, where the bacteria are contained within dental caries on the surface of the tooth or are caries contained within the tooth. At the frequencies used, microwave energy is selectively absorbed by the bacteria in the caries without causing damage to the tooth.

An apparatus using microwave energy to irradiate a tooth to treat dental caries; wherein the microwave energy is generated by a microwave generator, and applied to the tooth via a waveguide and an antenna; and wherein the microwave generator, the waveguide, and the antenna weigh between 0.5 pounds and 15 pounds, and in other embodiments, in the range of 2 to five pounds. The apparatus has a displacement volume of the microwave generator used for irradiating the tooth ranges from 6 cubic inches to 1440 cubic inches, and in still other embodiments in the range of 300 cubic inches to 400 cubic inches, where the microwave generator radiates microwave frequencies in the range of 26.5 to 40 GHz, preferentially in the range of 28 to 32 GHz. A gallium nitride power amplifier or a gallium arsenide power amplifier with a preamplifier driving the power amplifier are particularly well suited for use in the microwave generator.

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE INVENTION

Figure 1:
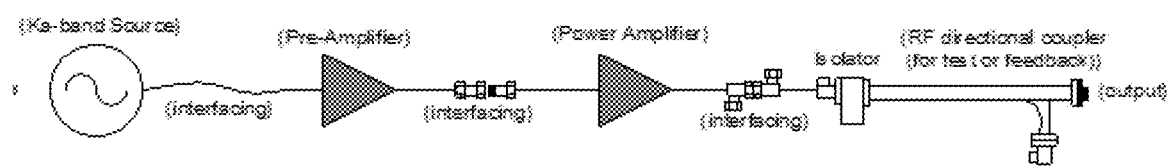
FIG. 1 is a schematic of an inventive apparatus microwave generator including a source, pre-amplifier, power amplifier, and an isolator.

A method and a device for treating dental caries using microwave irradiation is provided. Embodiments of the inventive device and method for the treatment of dental caries use microwave energy applied directly to teeth at frequencies that are lethal to the bacteria in caries, without being destructive to tooth tissues. The inventive technology will have a significant economic and health impact both through its anticipated adoption by the dental profession, which will lead to a reduction in traditional surgical interventions in the United States, as well by improving access to care for those with health disparities. Furthermore, the technology is designed to be usable by non-dental professionals such as school nurses. The inventive method and device is expected to be the first step in creating new approaches to the non-invasive management of caries that should reduce the cost of care.

With respect to the application of the inventive technology, the disclosed technology has utility for populations that would otherwise not receive care. As stated, low-income children with high rates of coronal caries or the institutionalized elderly having high rates of root caries could be treated by trained non-dental professionals with the device. In the institutionalized elderly, root caries (lesions on the roots of teeth exposed with aging) are often rampant, and technically difficult to treat, even by conventional surgical approaches. Given that minimal skill would be needed to treat caries using the inventive device, the technology would constitute an effective and low cost method of providing care to populations with untreated disease. With appropriate training, care could be provided in schools or nursing homes by non-dental professionals such as nurses and other health workers. In third world countries where there are no dentists, caries treatment using the proposed microwave technology could be provided by aid workers in regions where care would otherwise not be available. For example, the use of the device could "piggy back" onto vaccination programs, whereby children who line up with parents for the vaccination could be examined for caries and have their carious teeth exposed to the device when appropriate.

Compared to current strategies for the conservative management of caries, the technologies disclosed in this application are innovative because for the first time, practicing dentists will have a means of definitively and rapidly treating caries in a non-invasive manner in one visit via the chairside delivery of bacterially lethal doses of microwave energy. As an example, by exposing a tooth to microwave energy, bacteria in a lesion are killed and the acidogenic/aciduric properties of the lesion are altered. The local pH would be favorably modified, and a more predictable environment for rapid lesion remineralization both from the surface side of the lesion as well from its pulpal side should often preclude further intervention, The opportunities for the recurrence of caries in this scenario would be no greater than those for other intact mineralized surfaces. As another example, early stage lesions that may be on the borderline for a decision to treat by surgical means would be moved more confidently into the non-invasive treatment category by exposing the lesion to microwaves, with or without restoration. Patient compliance over months with longitudinal follow-up to insure that caries has been arrested may be eliminated or minimized.

Embodiments of the disclosed device and method provide a response to the need for a more effective and practical approach to the non-surgical management of dental caries. Embodiments of the novel apparatus have the capability of delivering chairside microwave energy at frequencies that are rapidly (in under a minute) and selectively absorbed by microflora inherent to superficial or deep caries without being destructive to the tooth itself. The irradiation, which can be focused, is used to kill caries-causing bacteria that are native to carious lesions in teeth. In conjunction with a coolant, there is no significant increase in the temperature of a tooth when the tooth is irradiated, nor does the microwave irradiation cause an adverse response of the cells of the pulp organ of the tooth. By irradiating the tooth with microwave energy, and by virtue of killing caries-causing bacteria, the local pH of the carious lesion contained within a tooth can be altered to favorably promote spontaneous remineralization of the tooth.

According to one aspect of the present invention, the irradiation is made using a microwave generator, which is in certain embodiments portable, a coaxial cable to transmit the microwave energy to an antenna, and an antenna, which is used to direct the microwave energy to a tooth. The microwave generator can contain a gallium nitride power amplifier to maximize power efficiency, and to reduce the size of the microwave generator. The coaxial cable provides for a flexible connection between the microwave generator and the antenna, which permits the antenna to be used at a distance from the microwave generator. The antenna can be focused or it can be an open-ended waveguide. The aperture of the antenna can be beveled to enable easier access to surfaces of teeth, or more preferably, can include a bend to facilitate microwave irradiation to all tooth surfaces. Furthermore, the impedance of the antenna is matched to that of tooth via the use of dielectric materials to maximize power transfer to the tooth. To irradiate the tooth, the antenna needs to be in contact with a tooth surface or some intermediary material whose impedance is matched to that of the tooth and which itself is in direct contact with the tooth. During irradiation, the tooth can be exposed to a coolant composed of air, water or a combination of both.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

In a specific embodiment, the inventive device includes of a microwave system, which in certain embodiments is portable, and which includes a control system operating in a range of −5 to +5 volts, a signal generator which operates in the range of −5 to 29 volts, an amplification system operating in the range of −5 to 30 volts, and which in certain embodiments contains a Gallium Nitride (GaN)-based amplifier, a feedback sub-system to monitor forward and reflected power, and a system for delivering the microwave energy to the tooth.

The system for delivering the microwave energy to the tooth includes a waveguide coupler, a waveguide or a coaxial cable connected to the waveguide coupler, an antenna coupled to either the waveguide or coaxial cable, and a system for providing a stream of either air or water, or a combination of air and water, to the area being irradiated. The microwave frequency generated is in the Ka band range of 26.5 GHz to 40 GHz, and in certain embodiments in the range of 28 to 32 GHz. It is noted that although a flexible waveguide can be used, the preferable means of connecting the antenna to the microwave emitter is by the use of a coaxial cable, which can have a 180 degree radius bend dimension in the range of three to four inches. This radius bend dimension is not absolute, as the function of the coaxial cable is to transmit the microwave energy to the antenna, without impeding the placement of the antenna into position in the mouth. If this function is achieved, the bend angle is not critical.

In the inventive embodiments, the antenna can be an open ended waveguide, or preferably, a modified waveguide transition having a dielectric fill. In a specific embodiment the preferable dielectric constant is K=9, which allows the radiating energy to make a smooth transition from the 50 ohms impedance of the antenna to the tooth impedance. The dielectric fill material can be granular and packed into the antenna, or it can be a machined solid state dielectric material that conforms to the geometry of the antenna, which can be inserted into the antenna. The antenna can taper to the desired aperture, which can vary in dimension. The dielectric material transitions the microwave energy so that the impedance of the antenna is matched to that of the tooth. The impedance matching maximizes the power absorbed by the tooth.

Furthermore, for the microwave energy to be effective in killing caries-causing bacteria, the caries in a tooth needs to be in the line of sight of the irradiating beam. Thus, the antenna can have apertures of varying sizes to accommodate various-sized carious lesions. Antennas with different sized apertures can be made by the gradual tapering of the waveguide antenna to the desired aperture size. In an embodiment, the antenna can have a bend at the radiating end to facilitate access of the antenna to all tooth surfaces when placing the antenna within the mouth. A bend angle that may be particularly useful is 70 degrees, as this angle will permit a straight-in entry of the antenna into the mouth with the radiating energy being directed at the tooth.

In certain embodiments, a method of enhancing the radiation of the evanescent mode waveguides (i.e. tapered down without dielectric loading) involves utilizing parasitic or material loadings at their apertures. To demonstrate the material loading technique, a Ka-band rectangle waveguide gradually tapered down from the original aperture size of 7.1×3.6 $mm^2$ and which incorporated a bend of 70 degrees to the long axis of the waveguide was modeled using a 3-D full-wave electromagnetic field simulator. The effect of illumination on caries using antennas having apertures of different dimensions was simulated. The antenna aperture sizes in the simulation were 4×3, 6×4, and 8×7 $mm^2$. To achieve good radiation, material loading at the smallest opening waveguide end was required. We used a 0.3 mm thick FR4 substrate ($\varepsilon r$=4.5) to reduce the return loss to less than 10 dB, which is an excellent result.

The device and method disclosed herein is based upon the recognition that microwave energy at a requisite frequency and power can selectively and safely kill caries-causing bacteria native to in situ caries. This realization is based on data generated have shown that (1) *Streptococcus mutans* selectively absorbs microwaves in the Ka band region; (2) radiation of *Streptococcus mutans* using Ka band microwaves kills the bacteria in less than a minute of exposure; (3) radiating bacteria seeded from caries that has been harvested from teeth kills the bacteria from the caries in less than a minute; (4) radiating a bolus of caries that has been harvested from teeth kills the bacteria native to caries; (5) using a model system, intervening tooth structure does not interfere with bacterial kills; and (6) when using a surface coolant, there is minimal surface temperature increase when a tooth is exposed to Ka band radiation at the time scale needed to kill bacteria. In addition, an animal study using rat incisors exposed to the microwave radiation shows no adverse histological response of pulp tissue to microwave irradiation. Examples of the device and method are described below.

EXAMPLES

Example 1: Microwave Device

A microwave system (FIGS. 1, 2), which in certain embodiments is portable, includes a control system operating in a range of −5 to +5 volts, a signal generator operating in the range of −5 to 29 volts, an amplification system operating in the range of −5 to 30 volts, and which in certain embodiments contains a Gallium Nitride (GaN) based amplifier operating in the range of Ka band range of 26.5 GHz to 40 GHz, and in certain embodiments in the range of 28 to 32 GHz, a feedback sub system to monitor forward and reflected power, and a delivery system for the microwave energy includes waveguide coupler, a waveguide or a coaxial cable and an antenna was designed and built. Multiple issues were considered in the design which included portability, the ability to deliver focused microwaves at useful frequencies, power output, antenna design, attenuation issues, signal, impedance matching and others. A discussion on the resolution of these design issues is beyond the scope of discussion here. Nonetheless, the result of this work is an operating device where a flexible waveguide or flexible coaxial cable (FIG. 3) is coupled to the microwave generator built to deliver microwaves in the Ka band range. The antenna design was a key consideration in developing the device. Two stock antennas operating at C band range and at Ka band range. The antenna 16 design was a key consideration in developing the device. Two stock antennas operating at C band range and at Ka band in the Industrial, Scientific, and Medical (ISM) band were initially developed. Theoretical simulations and practical measurements were performed both at the C and Ka band frequencies to determine optimal microwave absorption and thermal conduction characteristics of teeth and bacteria (Table 1). These simulations additionally provided guidance for the computerized design and construction of an antenna for dental use. Based on these studies, as well as the observation that microwave absorption in bacteria increases with short wave lengths while the reverse occurs for enamel and dentin, the Ka-band was selected for our work and a second antenna was designed having azimuthal directionality to target specific regions of a tooth. The original work used a straight waveguide antenna; however, to access some tooth surfaces in the mouth, a bend of approximately 70 degrees (FIG. 4) can be used to facilitate the delivery of microwave energy to those surfaces.

TABLE 1

Microwave absorption of enamel, dentin and caries. Volume = 1 mm³, power = 1 watt radiated

| Material | Freq (GHz) | Conductivity Simens/meter | Dielectric Constant | | Microwave Absorption dB per mm | % Power Absorption m/mm | Temperature Rise (° C.) per second |
|---|---|---|---|---|---|---|---|
| | | | Real | Imagined | | | |
| Enamel | 6 | .133 | 7.3 | .4 | .08 | 1.84 | .08 |
| | 10 | .167 | 7.0 | .3 | .103 | 2.34 | .11 |
| | 25 | .0014 | 7.0 | .001 | .00086 | .02 | 0 |
| Dentin | 6 | .333 | 7.0 | 1 | .206 | 4.62 | .21 |
| | 10 | | 6.7 | .7 | .245 | 5.5 | .25 |
| | 25 | | 6.6 | .001 | .00091 | .0022 | 0 |
| Caries | 6 | 3.17 | 25 | 9.5 | 1.02 | 20.9 | .98 |
| | 10 | 5.83 | 21 | 10.5 | 2.02 | 37.3 | 1.76 |
| | 25 | 13.90 | 12.5 | 10 | 6.03 | 75. | 3.54 |

Example 2: Bacterial Studies

Initial studies were undertaken to evaluate the variables involved in obtaining kill rates of *Streptococcus mutans*, the latter being the major pathogen in caries proliferation. The variables included frequency selection, antenna design, power output and time to obtain effective kill rates. Studies were initially conducted using direct microwave exposure of bacteria in microfuge tubes at various times to select out appropriate exposure parameters. Using these parameters, the studies were repeated in a tooth model where a bacteria-containing microfuge tube was placed internally to a depth of 4 mm. For these studies, the microwave antenna was brought into contact with side of the tooth, and the bacteria were radiated for various times, up to 90 seconds. Direct exposure of bacteria to $K_a$ band microwaves in media produced kill rates that approached 100% at relatively short periods of time (20 seconds.) Kill rates using the microfuge embedded in a tooth ranged from 33% at 15 second exposure to 98.3% at 90 seconds when using an open ended waveguide. When using a focused antenna, kill rates were routinely over 99% starting at 15 second exposures. For all experiments, colonies in control groups (no exposure) were 100% alive.

The effect of microwave energy on caries causing bacteria was determined by initially examining microflora in culture and then progressing to studies involving direct and indirect (sample behind tooth structure) exposure of caries harvested from teeth. For the microflora in culture, caries were harvested with consent from various patients needing routine treatment. After initial storage in sterile saline, the caries was subsequently recovered and transferred to sterile tryptic soy broth (TSB) for a series of dose-response studies. Individual caries fragments placed in TSB tubes were incubated and the TSB became turbid due to bacterial growth. Aliquots (n=5) of the turbid TSB were transferred to sterile microfuge tubes for either direct or indirect exposure to Ka band microwave energy. Equivalent untreated samples were used as controls. The exposed aliquots were then separately placed into new TSB tubes and allowed to incubate for another 24 h. After the incubating period, the TSB was streaked and CFU counts made to calculate bacterial kills. mean kill rate for five samples, as an example of our experiments, was 98.6% (SD=1.4%); all controls had 100% bacterial survival.

The general experimental methodology was repeated to next determine the effect of microwaves on bacteria in caries. After both direct and indirect exposure to the microwave energy, caries were placed into TSB. After 24 hours, the TSB was determined to be either being turbid or clear. In addition, for select samples, colony forming units (CFU) were determined by diluting the TSB containing caries and then streaking 10 microliters onto blood agar plates. Bacterial survival was calculated as % CFU's counted on a plate compared to an equivalent untreated control. In addition, Polymerase Chain Reaction (PCR) analysis was additionally performed on TSB samples for survival analysis of *S. mutans*, the bacteria specifically responsible for causing caries. The results (FIG. 6) overwhelmingly demonstrated that 100% of *S. mutans* were killed in each of the exposed samples while the kill rates for direct and indirect exposure were, respectively, 89 and 75%.

Example 3: Thermal Effect of Microwaves on Teeth

The rate at which the microwave energy is absorbed by teeth is dependent upon their microwave parameters. These include the real and the imaginary part of the complex dielectric constant as given by Eqn. 1:

$$\varepsilon\blacktriangle = \varepsilon' + j\varepsilon'' = \varepsilon' + j\cdot\sigma(\omega)/\omega \qquad (\text{Eqn. 1}),$$

where $\varepsilon'$ is the real part of the dielectric constant
$\varepsilon''$ is the imaginary part of the dielectric constant
j is the conductivity, and
$\omega$ is the operating frequency (radians)

As this energy is absorbed, it is thermally conducted into the tooth at a rate determined by its thermal conductivity. Thus the heating profile is dependent upon the microwave parameters, the thermal conductor parameters, the rate at which the microwave energy is deposited into the material, the operating frequency, and the impedance match between the antenna and the material. Theoretical calculations for these variables are shown in Table 1 above (note that 2 data points for conductivity for dentin are unavailable; however, the key data are shown in the last 3 columns).

The above calculations for enamel and dentin show an inverse correlation between wavelength, microwave/% power absorption and temperature. As frequency increases, power absorption and consequently temperature rise decreases. For caries, the inverse occurs; as wavelength increases, microwave/% power absorption and consequently temperature increase. Thus, these data would indicate that at higher frequencies, there is significantly greater microwave absorption and heat rise compared to enamel and dentin.

Figure 2:
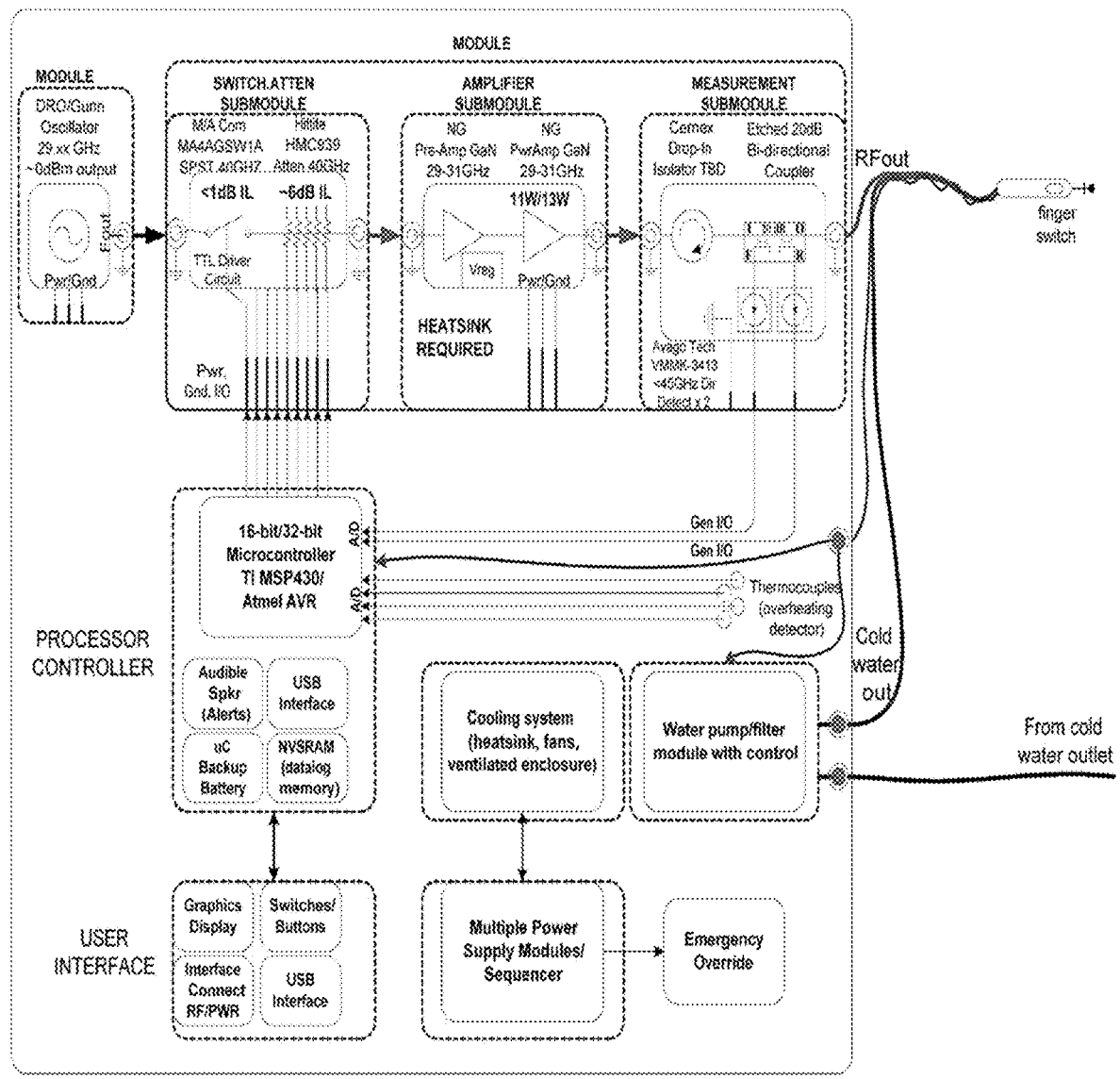
FIG. 2 is a schematic diagram of an inventive apparatus.
Figure 3:
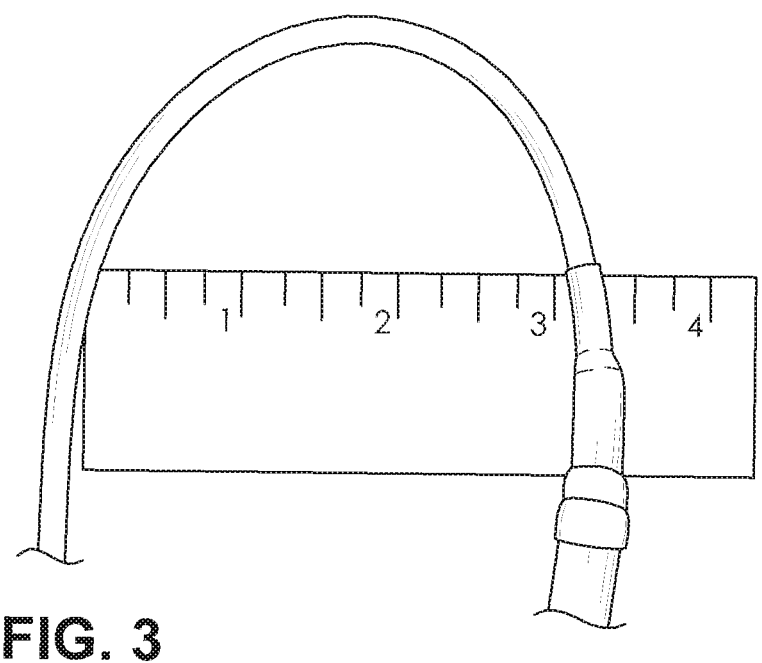
FIG. 3 is a photograph of a flexible radiofrequency (RF) cable as shown in the aforementioned figures.
Figure 4A:
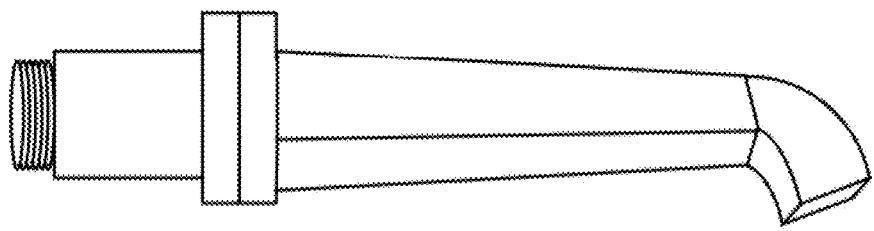
FIGS. 4A-4D are schematics of different tooth contacting antenna embodiments along with optional patient interfaces, co-axial cable adapters and cables.
Figure 4B:
Figure 4C:
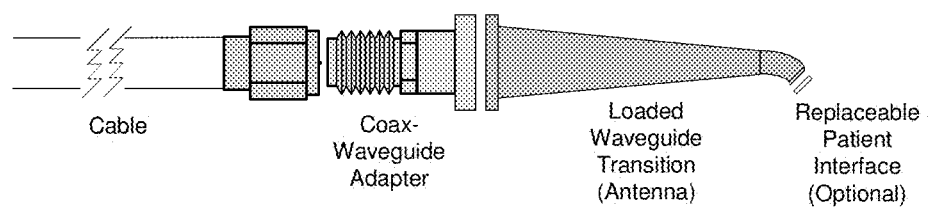
Figure 4D:
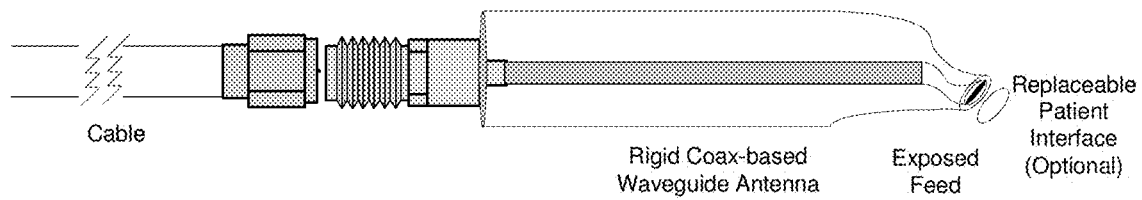
Figure 5:
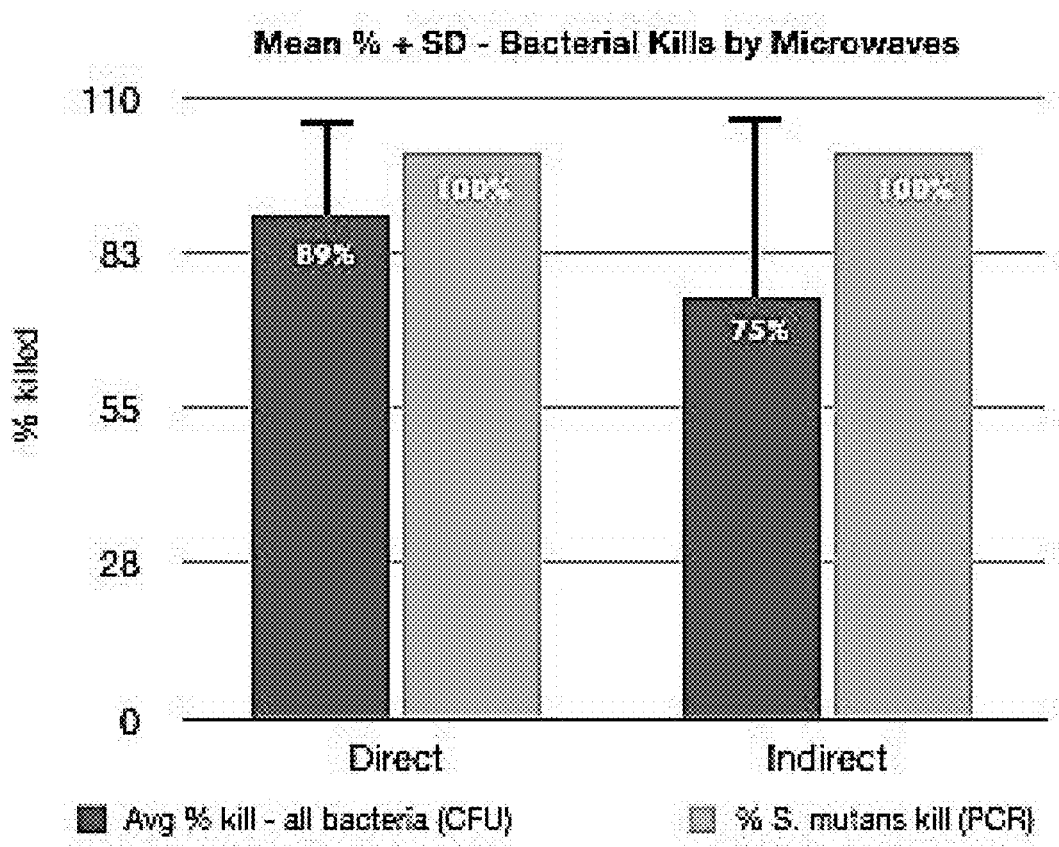
FIG. 5 are bar graphs of direct and indirect contact bacterial kill percentages under conditions detailed in the Examples.

To confirm the above theoretical computations, temperature measurements of molar teeth with and without occlusal preparations were made after exposure to the microwave radiation at ambient temperature. Subsequent measurements were taken every fifteen seconds. A portable, infrared thermal imager (Extech FLIR Systems IRC57) was used to measure temperature at the tooth's surface exposed to the microwave antenna. The summary data indicated that a 30 second exposure to the $K_a$ band frequency (which produced a 99% kill rate of bacteria when internally positioned in the tooth as seen in FIG. 2) resulted in an average surface temperature increase of prepared teeth (teeth with a "cavity") to 99.0 degrees F. (SD=4.6) and 102 degrees F. (SD=2.6) for intact teeth. These values were obtained using an air coolant on the tooth. It should be noted that the starting temperature of the tooth was the room ambient temperature.

Figure 6:
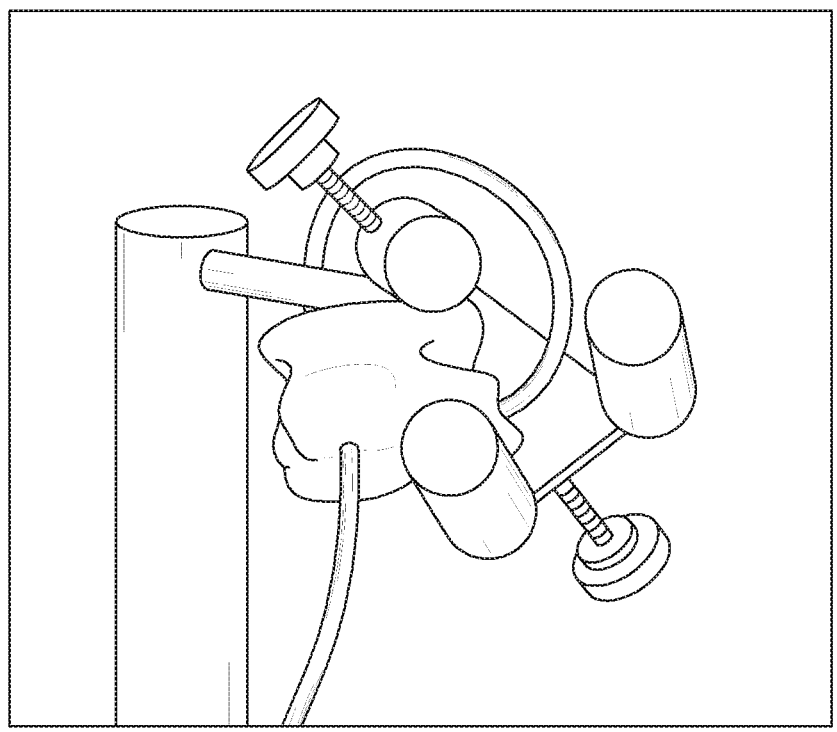
FIG. 6 is a photograph of a test rig simulating dental caries irradiation according to the present invention.

Experiments were further undertaken to evaluate high-frequency microwave energy on internal tooth temperature. For thermal testing, a channel to accommodate a thermocouple (TC) 42 was placed into teeth of varying sizes just above the pulp space and a catheter was inserted into the root opening. FIG. 6. shows the test configuration showing the tooth T positioned for microwave radiation, the catheter 44 connected to the root at the one end with a peristaltic pump with 37° C. water being pumped through the root into the pulp space on the other, and a thermocouple 42 positioned just above the pulp space of the tooth T. When pumping the 37° C. water, the internal temperature measured by the TC 42 was maintained at 36.7° C. The temperature increase after 60 s of microwave exposure with no coolant as measured by the TC was 7.8° C.; with water cooling, the average temperature increase for four tests was 1.3° C.

Structural effects of microwave exposure on native tooth structure were determined using microhardness tests, Raman spectroscopy and field emission scanning electron microscopy (FESEM). For Knoop hardness (KHN) determination, the average KHN for dentin sections (n=16) was obtained. After exposure to microwave radiation, the KHN was re-sampled adjacent to where the first sampling had been made. The mean overall KHN before and after microwave radiation was, respectively 73.2 (SD 41.0) and 82.2 (SD=61.5). Analysis using a paired t-test showed no significant differences in KHN before and after radiation.

Figure 7:
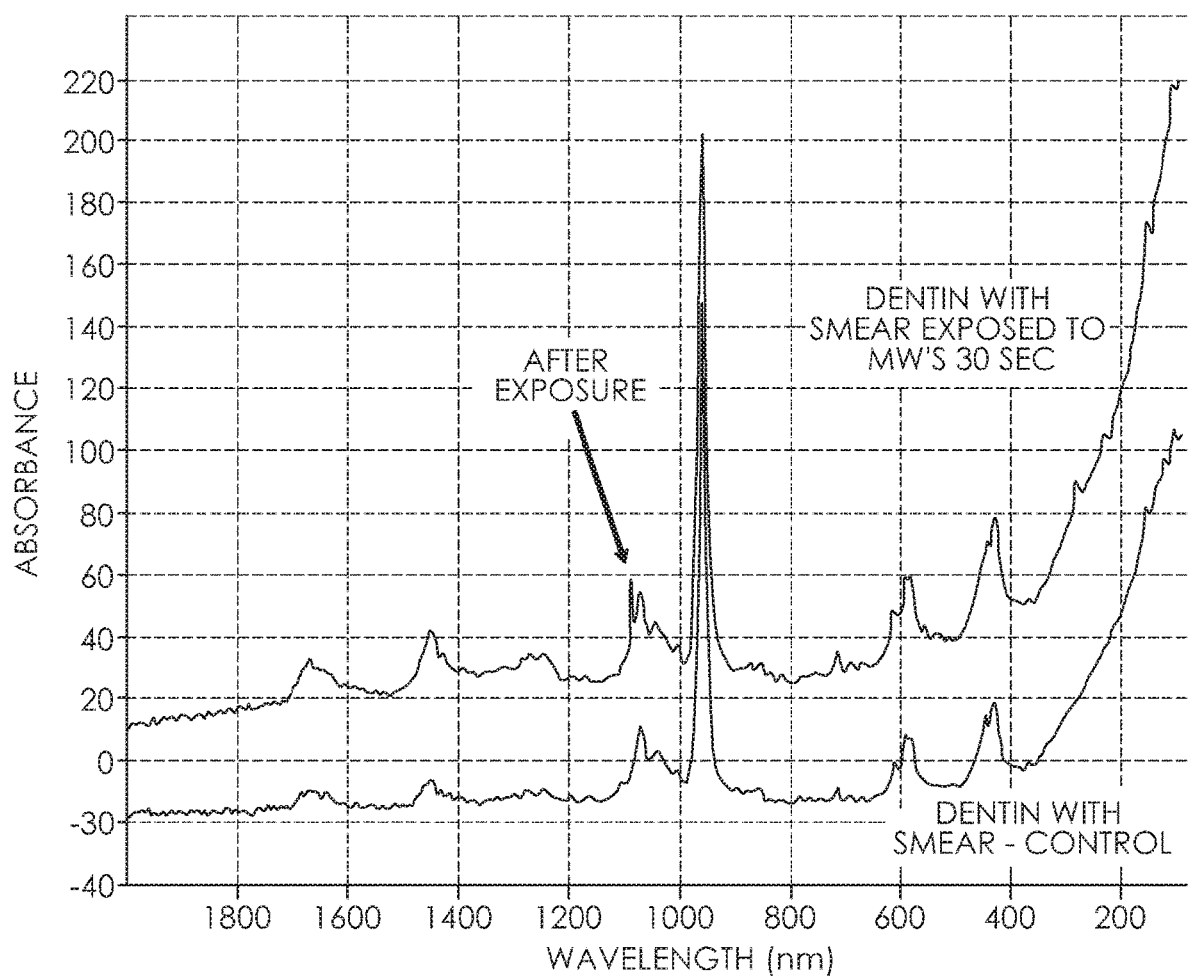
FIG. 7 are light absorption plots as a function of wavelength for dentin with smear exposed to microwave for 30 seconds and dentin control without microwave exposure.

Hydroxyapatite (HA; the mineral phase of dentin), bovine type I collagen (the protein phase) and dentin were each exposed to high frequency microwave radiation. Each of the samples plus a control were interrogated by Raman spectroscopy. In general, no differences in the chemical structure of HA crystals, bovine or dentin collagen were found in the spectra before and after microwave exposure. Each of the samples show normal variation of peak intensities (showing concentration differences) within the same tooth, but no variation in peak positions. Spectra of the dentin before and after exposure (FIG. 7) show good spectral congruence, with no shifts in peak position, indicating no effect for the microwave irradiation.

The one minor exception occurred in the mineral phase of dentin where a small peak appeared at the 1071 cm-1 after microwave exposure. This peak was assigned to a carbonate species, and was interpreted to indicate the release of carbonate from biological apatite, where its presence had been previously masked. Biological apatite is distinguished from hydroxyapatite inasmuch its apatite structure allows varied substitutions to occur for $Ca^{2+}$ without having a significant change in basic structure. One of these substitutions involves carbonate, which is present in low concentration. It is believe that this finding has no significant structural or clinical significance as manifested by there having been no significant differences in KHn values of the before and after microwave exposed dentin. In addition, the key bonding procedure used by dentists to adhere filling materials to teeth relies on an initial acid-controlled dissolution of mineral phase of dentin.

Figures 8A, 8B:
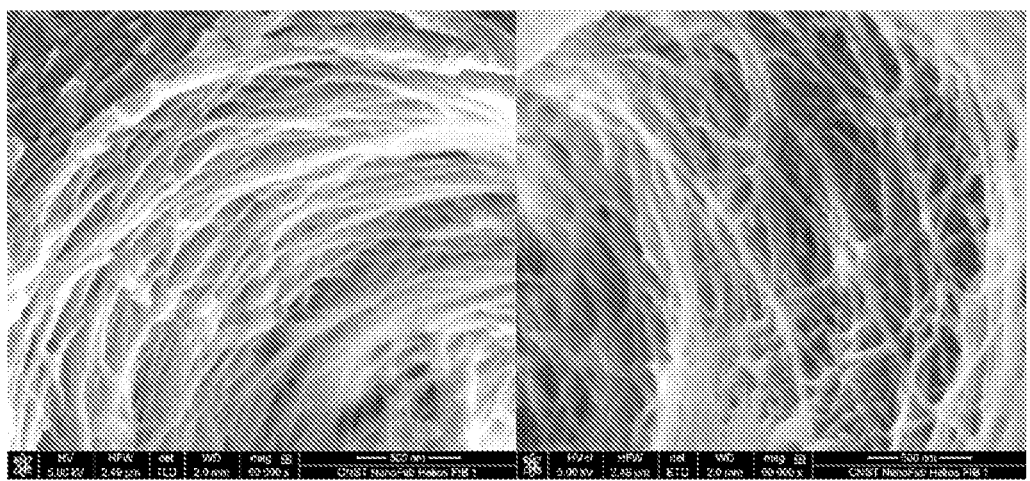
FIGS. 8(*a*) and (*b*) are micrographs of circumferential collagen networks in wall of dentinal tubule in a (a) control and (b) after exposure to microwave radiation (60000×).

For FESEM, HA crystals (NIST reference material), bovine tendon type I collagen and dentin were exposed to microwave radiation. The dentin was demineralized, fixed and sequentially dehydrated in a series of alcohols, with absolute ethanol being the final step. Samples, including controls, were mounted, coated and placed in an FESEM instrument and examined at magnifications up to 125,000×. No morphological differences were noted in the microwave-exposed samples compared to the controls for either the HA crystals, the bovine or dentin collagen. For the HA crystal examination, a number of irregularly shaped plates and crystals were observed in each of the samples, with no detectable differences being attributed to microwave exposure. For the bovine collagen, collagen fibrils are observed in the before and after exposure samples, displaying normal variation in morphology and cross linking to broader fibers. The 68 nm banding characteristic of type I collagen, typically observed in transmission electron microscopy, is not observed in any of the samples. Loss of banding would have been evidence of the denaturing of collagen due to microwave exposure. Fibrils are well organized in both images, and show their typical cross-linking patterns. Extensive cross-linking of the circumferential collagen networks are seen within the wall of the dentin tubules (FIG. 8). As with bovine collagen, there is no evidence of an effect for microwave radiation based on morphological observations. Again, banding is not observed in either image.

Example 4: Pilot Rat Study

A study to evaluate the effect of the microwaves at the cellular level was undertaken using rats. A study protocol was approved by the animal facility where the work was done. Rats were anesthetized, and incisors were randomly exposed to microwave radiation with focused antenna and coolant applied at the power setting used for ablating bacteria (about 2 watts) for either 0, 30 or 60 seconds. The rats were sacrificed after 1, 7 and 56 days.

At the time of sacrifice, the rat heads were severed and placed into formalin for 3 weeks. The relevant incisors with surrounding tissues were retrieved and demineralized. Serial sections were prepared for histological evaluation using H & E stain. Inflammatory response of the pulp, alveolar bone and periodontium was graded by a veterinarian pathologist using a subjective scale ranging from 0 (no finding present); 1 (minimal inflammation) and 2 (mild inflammation). No cellular changes were found in any of the pulp or bone tissues examined; the preponderance of findings in the soft tissues at any of the time scales were either none or a mild. The pathology report concluded that under the conditions of this study, there were no RF-associated microscopic findings involving incisors exposed to RF for 30 or 60 seconds at 24 hours, 7 days, or 56 days following treatment in this rodent model.

Based on the data calculated with respect to power absorption and temperature increase at the various frequencies (Table 1), the measurement of surface temperatures of teeth exposed to microwaves and the conclusion from the pilot rat study, within the limitations of this body of work, it can be concluded that there is no significant heat rise of teeth due to exposure to microwave irradiation, and that pulps remain viable without demonstration of pathology.

Conclusions: It is shown that (1) a portable device can be built to generate focused microwave energy at the Ka band frequency; (2) that the device can be used to directly irradiate teeth; (3) that Ka band microwave energy can kill bacteria directly and in tooth models when the bacteria are embedded within the tooth; (3) that the surface temperature increase of molar teeth after microwave irradiation is minimal; and (4) that within the limitations of a rat pilot study, there are no adverse effects of microwave irradiation on pulp tissues.

Terminology and Definitions

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

Terms used herein are intended as "open" terms (e.g., the term "including" should be interpreted as "including but not limited to," the term "having" should be interpreted as "having at least," the term "includes" should be interpreted as "includes but is not limited to," etc.).

Furthermore, in those instances where a convention analogous to "at least one of A,B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments or examples disclosed.

Any patents or publications mentioned in this specification are herein incorporated by reference to the same extent as if each individual publication was specifically and individually indicated to be incorporated by reference. The foregoing description is illustrative of particular embodiments of the invention, but is not meant to be a limitation upon the practice thereof.

REFERENCES

Ricketts D N, Kidd E A, Innes N, Clarkson J. Complete or ultraconservative removal of decayed tissue in unfilled teeth. Cochrane Database Syst Rev (2006) 3:CD003808.

Thompson V, Craig R G, Curro F A, Green W S, Ship J A. Treatment of deep carious lesions by complete excavation or partial removal: a critical review. *J Am Dent Assoc* (2008)139:705-12.

Banomyong D, Palamara J E, Messer H H, Burrow M F. Sealing ability of occlusal resin composite restoration using four restorative procedures. *Eur J Oral Sci* (2008) 116:571-8.

Hevinga M A, Opdam N J, Frencken J E, Bronkhorst E M, Truin G J. Microleakage and sealant penetration in contaminated carious fissures. *J Dent* (2007) 35:909-14.

Hevinga M A, Opdam N J, Frencken J E, Bronkhorst E M, Truin G J. Can caries fissures be sealed as adequately as sound fissures? *J Dent Res* (2008) 87:495-8.

Qvist, V. Sealing manifest occlusal caries in permanent teeth—2½-year results. *J Dent Res Issue* 90 (Spec Iss A): abstract number 0360, 2011 (www.dentalresearch.org).

Ribeiro D G, Pavarina A C, Dovigo L N, Palomari Spolidorio D M, Giampaolo E T, Vergani C E. Denture disinfection by microwave irradiation: a randomized clinical study. *J Dent* (2009) 37:666-72.

Yu Y, Chan W I, Liao P H, Lo K V. Disinfection and solubilization of sewage sludge using the microwave enhanced advanced oxidation process. *J Hazard Mater* (2010) 181:1143-7.

Vaid B. The destruction by microwave radiation of bacterial endospores and amplification of the released DNA. *J Applied Microbiol* (1998) 85: 115-22.

Viana P S, Machado A L, Giampaolo E T, Pavarina A C, Vergani C E. Disinfection of bovine enamel by microwave irradiation: effect on the surface microhardness and demineralization/remineralization processes *Caries Res*. (2010) 44:349-57.

Williams M R, Knaut M, Bérubé D, Oz M C. Application of microwave energy in cardiac tissue ablation: from in vitro analyses to clinical use. *Ann Thorac Surg* (2002):1500-05.

Goldberg S N, Gazelle G S, Mueller P R. Thermal Ablation Therapy for Focal Malignancy—A Unified Approach to Underlying Principles, Techniques, and Diagnostic Imaging Guidance. *Am J Roentgen* (2000) 174:323-31.

Stangel I. Unpublished data. 1992.

Nikawa Y, Hoshi N, Kawai K, Ebisu S. Study on dental diagnosis and treatment using millimeter waves. In: Microwave Theory and Techniques, *IEEE Transactions* (2000) 48:1783-88.

van Houte, J. Role of micro-organisms in caries etiology. *J Dent Res* (1994) 73:672-81.

Arndt G D, Byerly D, Sognier M, Stangel I. The chairside delivery of focused microwave energy for caries therapy. Conference paper submitted to the 2012 annual meeting of the American Association of Dental Research.

Garlick D. Report of microscopic data for histological response of rat incisors to microwave exposure, 2009.

The invention claimed is:

1. An apparatus for treating dental caries in a tooth comprising:
   a microwave generator capable of radiating microwave frequencies in the range of 26.5 to 40 GHz that are lethal to bacteria in caries on the tooth without being destructive to tissues that form the tooth;
   a waveguide or coaxial cable mechanically coupled to the microwave generator;
   an antenna with a proximal end in operable connectivity with the waveguide or coaxial cable and a radiating distal end, wherein the radiating distal end is adapted to deliver the radiating microwave frequencies by directly contacting the tooth or by contacting the tooth with an intermediary material having an impedance matching the tooth,
   where the distal end of the antenna has a bend at the radiating distal end of the antenna to facilitate access of the antenna to all tooth surfaces; and
   a cooling system for maintaining a temperature of the tooth being radiated to less than a 7° C. temperature increase after up to 60 seconds of microwave exposure, the cooling system comprising a water or air source, a pump, and a line, said line terminating in an opening directed to the tooth when the radiating distal end is in contact with the tooth to supply a coolant to the tooth being radiated via the antenna.

2. The apparatus of claim 1 wherein the microwave generator has a volume of from 6 cubic inches to 1440 cubic inches.

3. The apparatus of claim 1 wherein the antenna is comprised of an aperture having an output, wherein an output frequency radiated by the antenna is impedance matched to the tooth impedance.

4. The apparatus of claim 3 wherein the antenna is divided into multiple segments comprised of one or more dielectric materials capable of providing a near continuous impedance match from the antenna connected to the waveguide or the one or more coaxial cables, and through the antenna aperture into the radiated tooth containing caries.

5. The apparatus of claim 1 further comprising a control system operable in a range of −5 to +5 volts and comprising:
   a signal generator operable in the range of −5 to 29 volts;
   an amplification system operable in the range of −5 to 30 volts.

6. The apparatus of claim 1 wherein the coolant is air, water, or a combination thereof.

7. The apparatus of claim 1 wherein the bend of the antenna has a bend angle of 70 degrees.

8. The apparatus of claim 1 wherein the antenna further comprises a modified waveguide transition having a dielectric fill material, where the dielectric fill material transitions the microwave energy so that the impedance of the antenna is matched to that of the tooth.

9. The apparatus of claim 8 wherein the dielectric fill material is granular and packed into the antenna.

10. The apparatus of claim 8 wherein the dielectric fill material is a machined solid state dielectric material that conforms to the geometry of the antenna and is inserted into the antenna.

11. The apparatus of claim 8 wherein the dielectric fill material is suitable to allow the radiating energy to make a smooth transition from a 50 ohms impedance of the antenna to the tooth impedance.

* * * * *